April 9, 1957 W. A. WARRINER Plant Pat. 1,588
ROSE PLANT
Filed Aug. 22, 1956
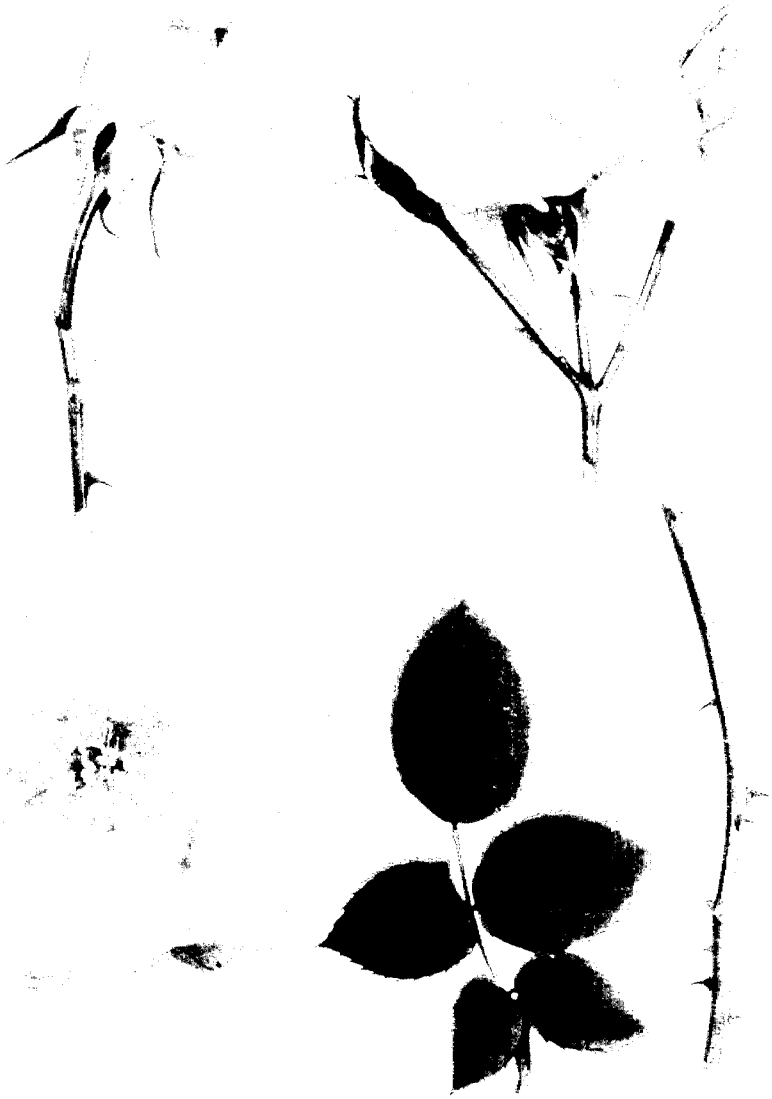
INVENTOR
William Arundale Warriner
By Orville M. Kile
Plant Patent Agt.

United States Patent Office

Plant Pat. 1,588
Patented Apr. 9, 1957

1,588

ROSE PLANT

William A. Warriner, Pico, Calif., assignor to Howard & Smith, Inc., Montebello, Calif.

Application August 22, 1956, Serial No. 605,681

1 Claim. (Cl. 47—61)

My present invention relates to a new and distinct variety of hybrid Floribunda rose plant and originated as a seedling which resulted from definite breeding efforts carried on by me in nurseries in Southern California, in the course of my regular duties.

Parentage of the new rose variety is Tom Breneman (Plant Patent #986)×Fashion (Plant Patent #789). The new variety somewhat resembles its parent "Fashion," but differs considerably, particularly in growth and the color and fragrance of the flower.

I have assexually reproduced this new variety by means of budding, at the Southern California location, and find that its distinguishing features appear to be permanent.

The accompanying illustration is a colored photograph showing several specimens of the flower of this new variety, together with a separate leaf and portion of stem—all in approximately their true colors, making allowances for photographic shadows.

In the following detailed description, color plate numbers refer to Ridgway's Color Standards and Nomenclature, and color names without plate references indicate the ordinary dictionary meaning of the term.

*The plant*

Growth habit: Vigorous upright bush, attaining a height of 2 to 3 feet.

Blooming habit: Prolific producer of good flowers continuously throughout the season.

Stems:

*Strength.*—Slender but strong.

*Color.*—Morocco Red, shading to maroon (both Plate I).

*Thorns.*—Few; slightly downward-curving; 1/8 to 3/16 inch in length, and approximately Oxblood Red (Plate I).

Foliage:

*Quantity.*—Abundant.

*Type.*—Odd-pinnately compound, with 5 to 7 leaflets.

*Shape.*—Oval-apiculate; sharply and finely serrated.

*Size.*—Terminal leaflet averages 3/4 inch by 1 1/8 inch, with lateral leaflets progressively smaller toward the stem.

*Color.*—Spinach Green (Plate V).

*Texture.*—Corriaceous.

*Stipules.*—Narrow; pointed.

*Rachis.*—Strong; free of spines.

*Disease resistance.*—No disease has ever been noted, although grown fairly near varieties which had a small amount of blackspot.

*The flower*

Bud:

*Size.*—Medium. Half-open bud is 1 1/8 inches to 1 3/4 inches in length.

*Shape.*—Conical.

*Color.*—When color first shows, Begonia Rose; bud beginning to unfurl, Geranium Pink (Plate I); half-open flower, Eosine Pink, with edges of petals slightly darker. (All Plate I).

*Peduncle.*—Strong; 1 1/2 to 3 1/2 inches in length; same color as stems.

*Sepals.*—Prominent; mostly simple but slightly branched; 7/8 to 1 inch long; reflex early.

Bloom:

*Borne.*—Both singly and irregularly clustered.

*Size.*—From 2 1/2 to 3 1/2 inches in diameter, with a depth of approximately 1 1/2 inches.

*Form.*—High centered at first. Later, opens loosely but is never flat, with outer petals reflexed and inner petals wide open, revealing the center of a large number of stamens and pistils.

*Petalage.*—From 18 to 24 petals.

*Color.*—Eosine Pink (Plate I), shading to Hermosa Pink (Plate I).

*Fragrance.*—Very abundant tea fragrance.

*Longevity.*—Average.

Petals:

*Shape.*—Obovate-cuneate.

*Substance.*—Heavy.

*Size.*—Average is 1 1/2 inches wide by 1 3/4 inches long.

*Edge.*—Mostly smooth; undulate, with inner petals of ten having a ruffled appearance.

*Behavior.*—Persisting.

Reproductive organs:

*Pistils.*—Numerous; bunched. Styles—strong and approximately 1/8 inch long. Stigmas—prominent. Dark yellow.

*Stamens.*—Very numerous; surrounding pistils. Filaments—strong and slightly curved inward; irregular lengths and longer than styles. Anthers—large; bright yellow.

*Pollen.*—Average amount.

*Receptacle.*—Rounded; slightly concave.

*Comparison*

The variety which my new variety most resembles is one of its parents—Fashion (Plant Patent #789), but it differs from that variety principally in the following respects.

1. My new variety has a more upright growth than Fashion.

2. The flower of my variety is lighter and a truer shade of pink.

3. The flower of my variety has a more abundant fragrance.

4. The petals of the flowers of my variety have greater substance and do not lie as flat in the open flower.

5. My new variety has a greater number of stamens and pistils composing the center of its flower.

Having thus disclosed my discovery, I claim:

The new and distinct variety of hybrid Floribunda rose plant, substantially as herein shown and described, characterized particularly by its upright growth; its habit of prolifically bearing flowers both singly and in clusters; and the novel combination of characters of its flower, which has intense fragrance, light pink color, and graceful, perfect high-centered form, enhanced by substantial petals and large, bright-yellow center.

No references cited.